(12) United States Patent
Barshinger et al.

(10) Patent No.: US 7,305,885 B2
(45) Date of Patent: Dec. 11, 2007

(54) METHOD AND APPARATUS FOR PHASED ARRAY BASED ULTRASONIC EVALUATION OF RAIL

(75) Inventors: James Norman Barshinger, Scotia, NY (US); Sandeep Kumar Dewangan, Bangalore (IN); Sivaramanivas Ramaswamy, Bangalore (IN); Jian Li, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 141 days.

(21) Appl. No.: 10/955,804

(22) Filed: Sep. 30, 2004

(65) Prior Publication Data

US 2006/0065055 A1  Mar. 30, 2006

(51) Int. Cl.
*G01N 29/06* (2006.01)
*G01N 29/265* (2006.01)

(52) U.S. Cl. .............................. 73/602; 73/611; 73/633
(58) Field of Classification Search ................... 73/602
See application file for complete search history.

(56) References Cited

U.S. PATENT DOCUMENTS

| | | | |
|---|---|---|---|
| 4,174,636 A | | 11/1979 | Pagano ........................ 73/636 |
| 4,180,790 A | * | 12/1979 | Thomas ......................... 367/7 |
| 4,974,558 A | * | 12/1990 | Katakura et al. ........... 600/447 |
| 5,119,342 A | * | 6/1992 | Harrison et al. ............... 367/7 |
| 5,520,186 A | * | 5/1996 | Deitrich ...................... 600/437 |
| 5,522,265 A | | 6/1996 | Jaeggi .......................... 73/625 |
| 5,617,862 A | * | 4/1997 | Cole et al. .................. 600/459 |
| 5,804,731 A | | 9/1998 | Jaeggi .......................... 73/636 |
| 2002/0065610 A1 | | 5/2002 | Clark et al. ................... 702/35 |

FOREIGN PATENT DOCUMENTS

EP    1132735 A1    9/2001

* cited by examiner

*Primary Examiner*—Herzon Williams
*Assistant Examiner*—Rose M Miller
(74) *Attorney, Agent, or Firm*—Fletcher Yoder

(57) ABSTRACT

In accordance with one embodiment, the present technique provides a testing apparatus for testing material integrity of an object. The exemplary testing apparatus includes a phased array transducer, which is disposed external to the object. The phased array transducer is configured to transmit a first set of ultrasonic signals and to receive a second set of ultrasonic signals. The testing apparatus further includes logic circuitry coupled to the phased array transducer. The logic circuitry is configured to dynamically control apertures for transmitting the first set of ultrasonic signals and receiving the second set of ultrasonic signals based on a region of interest and a testing speed.

13 Claims, 7 Drawing Sheets

METHOD AND APPARATUS FOR PHASED ARRAY BASED ULTRASONIC EVALUATION OF RAIL

BACKGROUND

The present invention relates generally to a technique for inspecting materials and testing material integrity. Particularly, the present technique relates to methods and apparatus for testing the integrity of rails in railroad systems using phased array based ultrasonic techniques.

Detecting the presence of defects in rails can assist maintenance technicians, for example, in predicting and mitigating the likelihood of rail malfunctions due to defects, for instance. By way of example, commonly occurring defects in the rail and/or railheads of railroad transportation systems are horizontal defects, transverse defects and bolt-hole defects. Horizontal defects, such as shelling and horizontal split-heads, are generally transverse and sometimes parallel to the longitudinal axis of the rail. Conversely, transverse defects are generally perpendicular to the longitudinal axis of the rail. Another general category of defects is bolthole defects, which generally occur near the boltholes of the rail. Under certain conditions, horizontal and transverse defects as well as bolthole defects can propagate under the fatigue of cyclic use. Unfortunately, these defects or cracks in the rail can increase the likelihood of failure or malfunction of the rail and/or railhead, leading to undesirable maintenance costs and downtimes, for instance.

In many instances, rail inspections are performed using an ultrasonic transducer mounted to an inspection vehicle. For example, one ultrasonic testing technique employs a single ultrasonic transducer attached to a sliding fixture, which, in turn, is mounted to a moving inspection vehicle. In another inspection method that is generally known as a "wheeled-probe system" an ultrasonic transducer is placed within a small diameter of a fluid filled inspection wheel that, in turn, is mounted to a moving inspection vehicle. In such a system, the fluid provides a medium for the ultrasonic waves to travel from the transducer and into the rail.

In traditional wheeled-probe systems, the time-to-flight, i.e., the period of time required for ultrasonic wave to leave the transducer, reflect from a base of the rail and return to the sensing device, is approximately 180 microseconds. Accordingly, to increase the likelihood that the transmitted wave returns to the sensing device, the speed of travel (i.e., scan speed) of the wheel-probed system is limited to approximately 35 miles per hour (mph). That is to say, if scan speeds exceed 35 mph, losses of reflected ultrasonic signals will dramatically increase, because the ultrasonic transducers will have traveled past the inspection area before the reflected ultrasonic signals can reach or return to the transducer. Hence, traditional testing techniques are limited at the speed at which testing can be performed. Unfortunately, limited testing speeds can lead to unwanted delays in track testing that, in turn, can lead to track closures, for instance.

Additionally, traditional techniques call for focusing and directing a generated beam by mounting the ultrasonic transducers at fixed angles with respect to the rails. Unfortunately, angularly maintaining the ultrasonic transducers with respect to the rail decreases the cross-section coverage area of the ultrasonic transducers. In turn, the probability of detecting oriented defects is also decreased, because of reduced area.

Thus, there exists a need for methods and apparatus for performing high-speed inspections to detect defects in the rails and to determine the integrity of such rails.

BRIEF DESCRIPTION

Briefly, in accordance with one embodiment, the present technique provides a testing apparatus for testing material integrity of an object. The exemplary testing apparatus includes a phased array transducer, which is disposed external to the object. The phased array transducer is configured to transmit a first set of ultrasonic signals and to receive a second set of ultrasonic signals. The testing apparatus further includes logic circuitry coupled to the phased array transducer. The logic circuitry is configured to dynamically control apertures for transmitting the first set of ultrasonic signals and receiving the second set of ultrasonic signals based on a region of interest and a testing speed.

In accordance with another embodiment of the present technique, an exemplary method for testing material integrity of an object is provided. The method includes controlling a first aperture dynamically for transmitting a first set of ultrasonic signals towards a region of interest. The method further includes controlling a second aperture dynamically to receive a second set of ultrasonic signals from the region of interest. Advantageously, the use of dynamic apertures facilitates increases in testing speeds and, as such, facilitates improved testing.

DRAWINGS

These and other features, aspects, and advantages of the present invention will become better understood when the following detailed description is read with reference to the accompanying drawings in which like characters represent like parts throughout the drawings, wherein.

Figure 7:
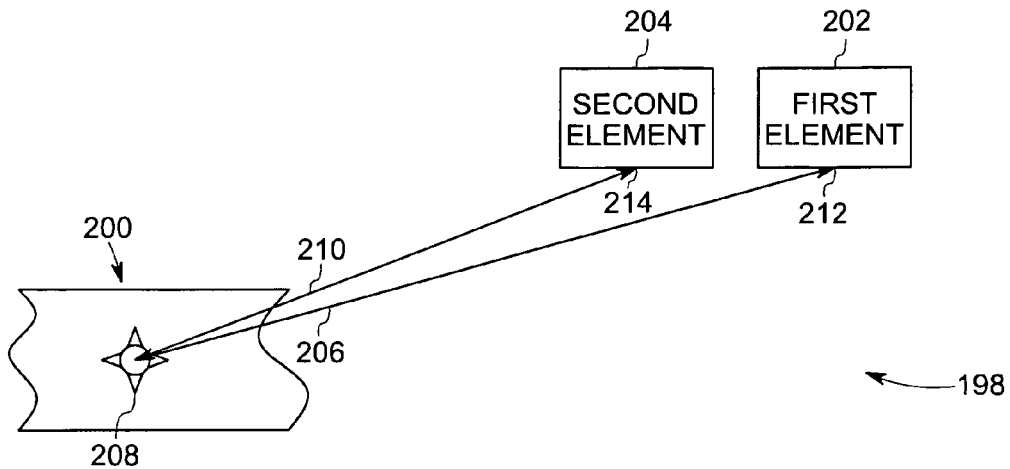
FIG. 7 is a diagrammatic representation of a testing apparatus for performing dynamic focusing for testing material integrity of an object, in accordance with an exemplary embodiment of present technique.
Figure 8:
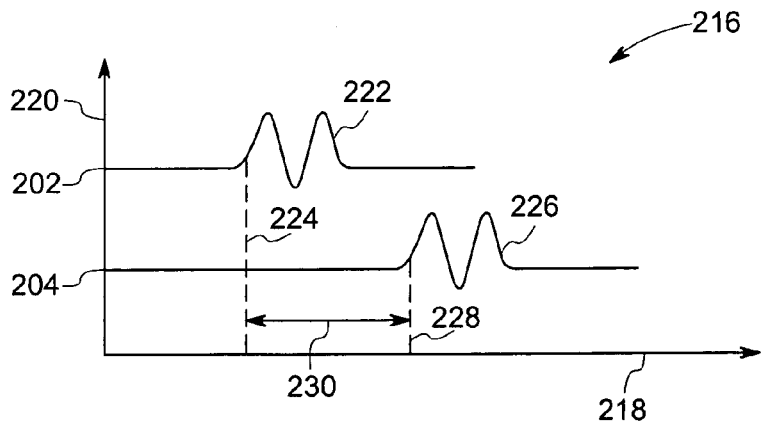
Figure 9:
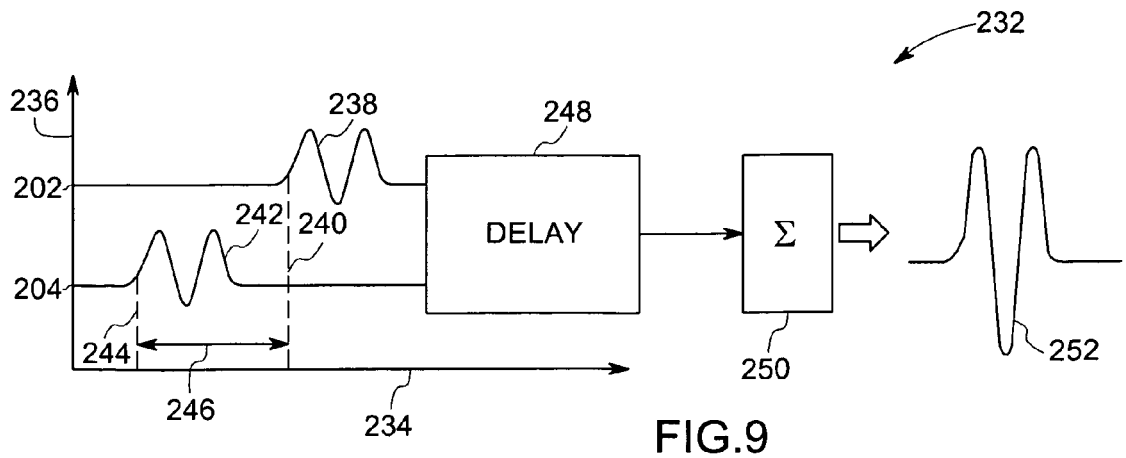
Figure 10:
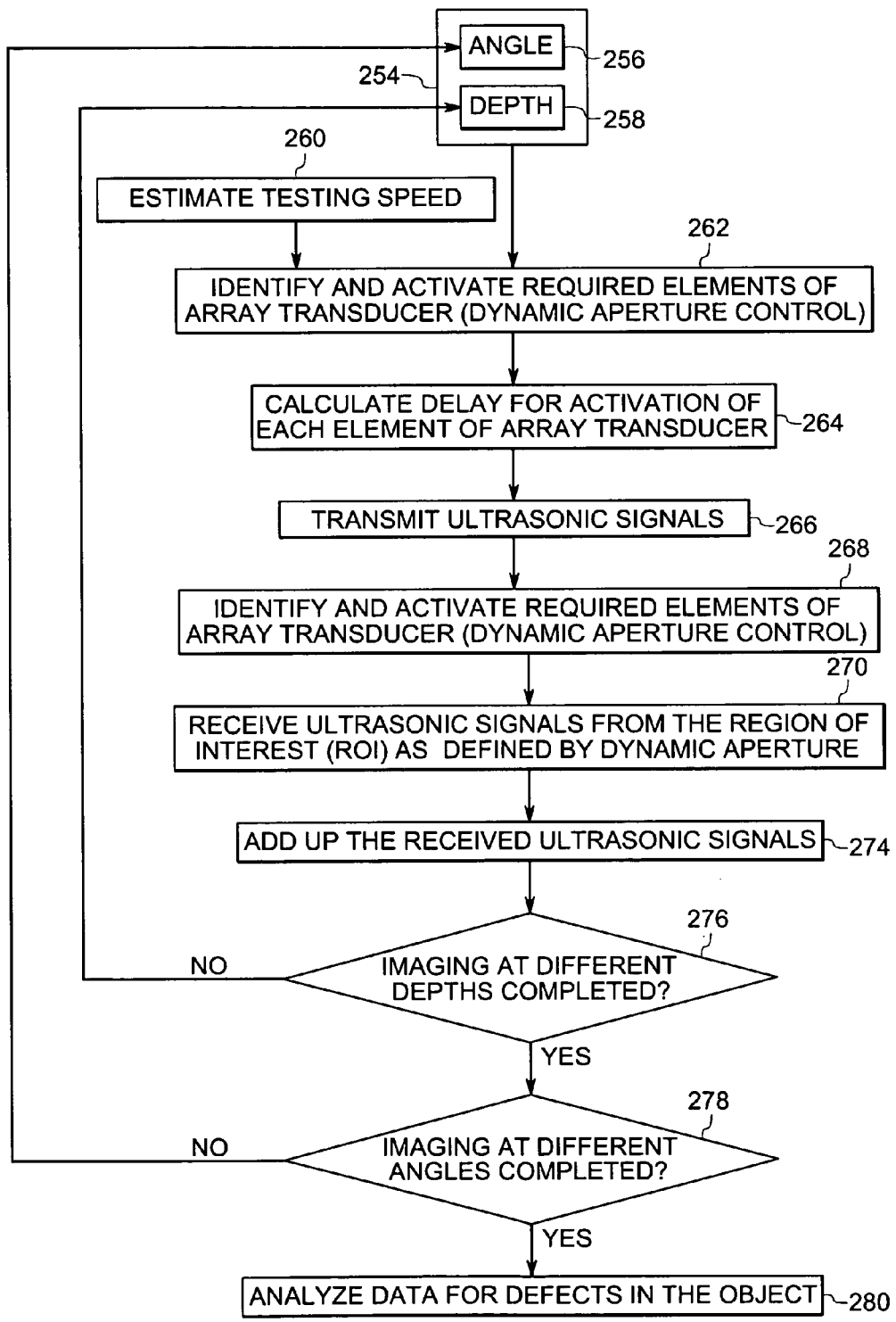
Figure 11:
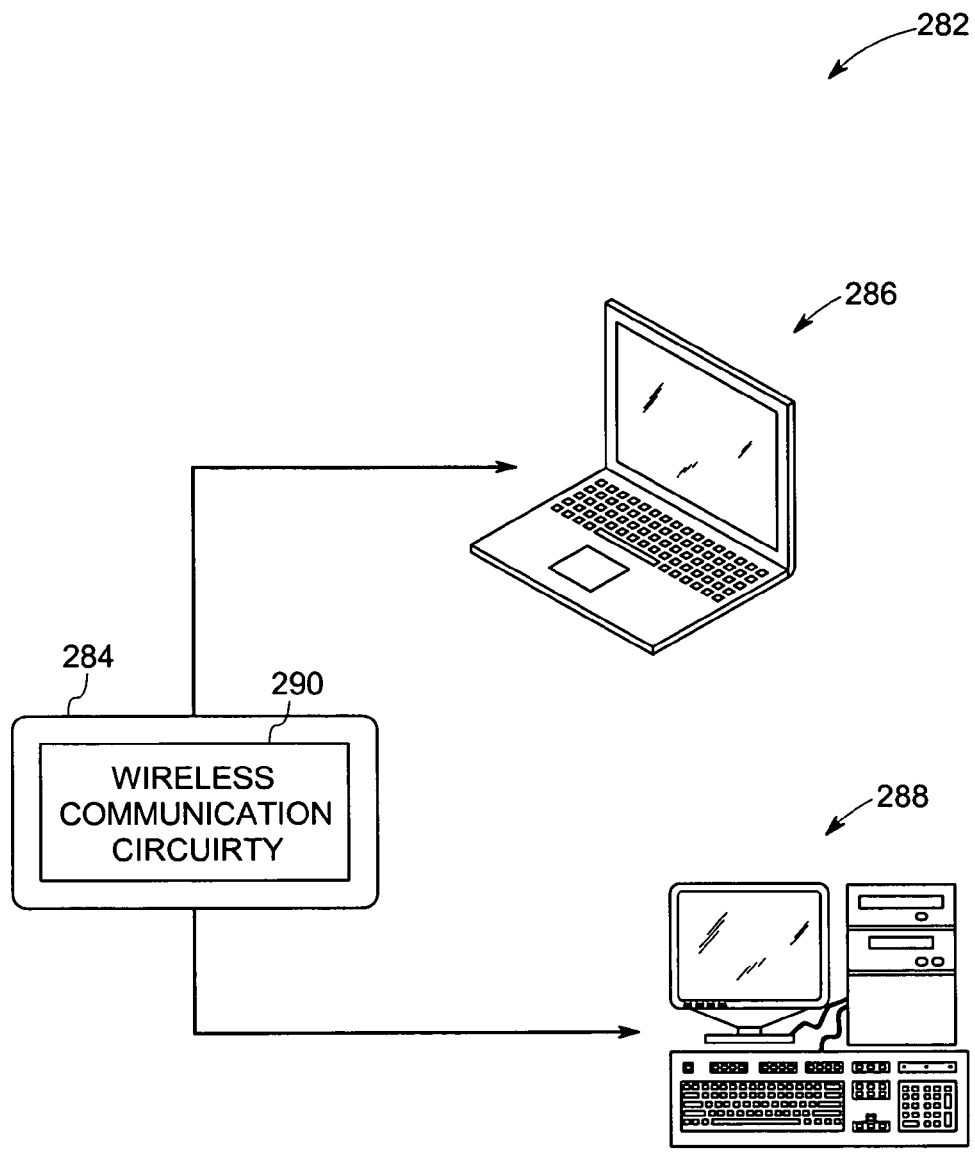

FIG. 8 graphically represents transmission of ultrasonic signals by phased array transducer elements of FIG. 7 with time delay, in accordance with certain aspects of present technique;

FIG. 9 graphically represents reception of ultrasonic signals by phased array transducer elements of FIG. 7 with time delay, in accordance with certain aspects of present technique;

FIG. 10 is a flowchart illustrating an exemplary process for detecting defects in a rail, in accordance with aspects of present technique; and FIG. 11 is a diagrammatic representation of a remote monitoring and field monitoring arrangement, in accordance with an exemplary embodiment of present technique.

DETAILED DESCRIPTION

The present technique is directed towards testing the integrity of an object and for detecting defects in the object. Although following discussion focuses on testing apparatus and methods for rails in railroads using phased array transducers, those skilled in the art will recognize in light of the following discussion that the present technique is applicable to a wide variety of testing environments and settings. For example, the present technique can be applied for testing of plates, bars and support structures, to name but a few applications. These techniques utilize transmitting ultrasonic signals into the object, receiving reflected ultrasonic signals from the object and analyzing the received ultrasonic signals for determining defects in the object. Furthermore, the following discussion merely present exemplary embodiments of the present technique, and is not intended to limit the scope of the appended claims to the discussed embodiments.

As a preliminary matter, the definition of the term "or" for the purpose of the following discussion and the appended claims is intended to be an inclusive "or." That is, the term "or" is not intended to differentiate between two mutually exclusive alternatives. Rather, the term "or" when employed as a conjunction between two elements is defined as including one element by itself, the other element itself, and combinations and permutations of the elements. For example, a discussion or recitation employing the terminology "A" or "B" includes: "A", by itself "B" by itself and any combination thereof, such as "AB" and/or "BA."

Figure 1:
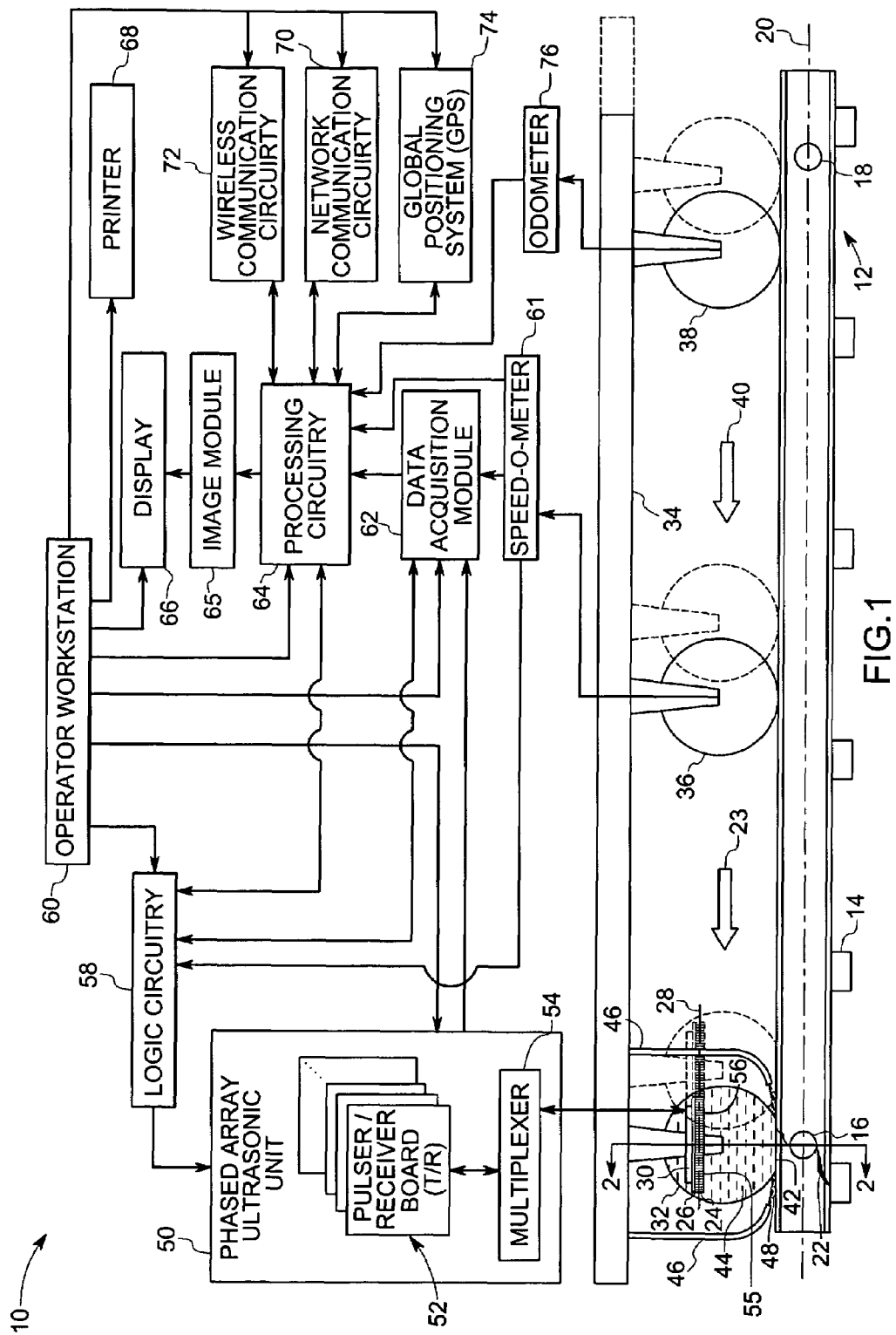
FIG. 1 is a diagrammatic representation of a testing apparatus using a phased array transducer for testing a rail, in accordance with an exemplary embodiment of present technique.

Turning now to the drawings, and referring first to FIG. 1, an exemplary embodiment of a testing apparatus 10 for detecting defects in a rail 12 is illustrated diagrammatically. As depicted, a set of railroad ties 14 acts as spacers between two parallel rails. The rail 12 includes boltholes 16 and 18, which are used for connecting a series of rails. The present technique is applicable to any number of rail constructions, such as continuous welded rails (CWR), and this present rail construction is only but one example. The longitudinal axis of the rail 12 is denoted by 20. The defect 22 is a combination of a bolthole defect and a transverse defect. During operation, as described further below, the testing apparatus 10 travels in a direction of travel, that is, generally parallel to the longitudinal axis 20 of the rail, as represented by directional arrow 23.

As illustrated, the testing apparatus 10 includes a phased array transducer 24 disposed externally with respect to the rail 12. Phased array transducer is a real time ultrasound electronic array transducer assembly, including one-dimensional or two-dimensional array of small transducer elements, where the ultrasound beam is both steered and focused by electronic means. The phased array transducer 24 includes ultrasonic transducer elements arranged in a housing 26 with respect to one another. In particular embodiments the transducer elements comprise piezo-electric devices, however other kinds of devices are also envisaged. In the present embodiment, each transducer element has a length, which is measured in the direction of the longitudinal axis of the rail that is less than its width, which is measured in a direction transverse to the longitudinal axis of the rail.

The transducer elements transmit and receive ultrasonic signals to and from the rail 12 to facilitate the detection of defects in the rail 12. Operations of each transducer element or a group of elements of the phased array transducer 24 are under the direction of a phased array ultrasonic unit, as discussed further below. In the present embodiment, the longitudinal axis 28 of the phased array transducer 24 is generally parallel to the longitudinal axis 20 of the rail 12.

Selected transducer elements of the phased array transducer 24 are collectively activated to transmit ultrasonic signals to define a transmit aperture. Similarly, another set of selected transducer elements of the phased array transducer 24 are activated to receive ultrasonic signals to define a receive aperture. The transmit aperture and the receive aperture, in the embodiment, are controlled by selectively activating, for transmission or receipt, selected elements of the phased array transducer 24. The embodiments provide ultrasonic signals at angles of transmission and angles of reception of ultrasonic signals by controlling firing or activation and reception patterns of the elements of the phased array transducer 24. Furthermore, an exemplary embodiment of the present technique facilitates control of ultrasonic signals to modify the focal depth of the ultrasonic signals to focus on different depths in the rail 12. That is to say, the activation pattern of the transducer element facilitates the focusing and directing of the produced signals. In the embodiment, the longitudinal axis 28 of the phased array transducer generally extends in the direction of the longitudinal axis 20 of the rail.

The phased array transducer 24 is mounted to a bracket 30 of a testing wheel 32, which is mounted to a carrier structure 34. Additionally, the testing apparatus 10 includes wheel assemblies 36 and 38 that support the carrier structure 34 and that facilitate movement along the rail 12. In the present figure, objects illustrated in dashed line represent positions of the testing apparatus 10 at a first time, while the solid lines illustrate the testing apparatus 10 at the second time after the first time. The carrier structure 34 facilitates the movement of the phased array transducer 24 in a testing direction 40, which is generally in the direction the longitudinal axis 20 of the rail 12. An outer surface of the testing wheel 32 is formed of a flexible material such as rubber, to improve the resiliency of the assembly. The testing wheel 32 is coupled to the carrier structure 34 in such a way that it has a small flat portion 42, due to compression where the testing wheel 32 contacts the rail 12. This flat portion 42 increases an area of contact between the testing wheel 32 and the rail 12 and, hence, facilitates an increase in the quantity of ultrasonic signals between the phased array transducer 24 and the rail 12. Advantageously, the testing wheel 32 is filled with a water based couplant 44, which provides a conduit for improved transmission of ultrasonic signals between the phased array transducer 24 and the rail 12. The carrier structure 34 includes a pair of tubes or nozzles 46 to apply the couplant 48, such as water, to improve transmission of the ultrasonic signals between the testing wheel 32 and the rail 12. The couplant 48 between the testing wheel 32 and the rail 12 also facilitates dissipation of heat due to friction between the testing wheel 32 and the rail 12. Although only one testing wheel 32 is illustrated, the testing apparatus 10 can include more than one testing wheel 32. Furthermore each testing wheel 32 may also support more than one phased array transducer 24 to test the material integrity of the rail 12 at different angles and/or depths.

The phased array transducer 24 is electrically coupled to a phased array ultrasonic unit 50. The phased array ultrasonic unit 50 includes pulser/receiver boards 52 and a multiplexer 54. The pulser/receiver boards 52 produce a high-voltage spike that excites selected transducer elements 55 of the phased array transducer through multiplexer 54 to generate ultrasonic signals. The pulser/receiver boards 52 and the multiplexer 54, by exciting selected elements of the phased array transducer to transmit coordinated ultrasonic signals, define the transmitting aperture of the phased array transducer 24. Similarly the pulser/receiver boards 52 and the multiplexer 54 may also define the receive aperture by activating selected elements 56 of the phased array transducer 24 for receiving ultrasonic signals.

The testing apparatus 10 includes logic circuitry 58 that is in communication with the phased array ultrasonic unit 50. The logic circuitry comprises hardware and/or software components and receives inputs from various sources to direct the phased array ultrasonic unit 50 in response to these inputs. The logic circuitry 58 can be located on the testing apparatus 10 or can be located remotely with respect to the carrier structure 34, as discussed further below. The logic circuitry 58 receives commands and instructions, such as a selected region of interest in the rail, from an operator workstation 60, for example. The operator workstation 60 includes input devices such as a keyboard, a mouse, and other user interaction devices. The operator workstation 60 can be used to customize various settings for detecting defects in a rail and to effect system level configuration changes. Hence, an operator controls the testing apparatus 10 via the operator workstation 60. Additionally the logic circuitry 58 receives inputs, such as speed of the testing apparatus 10, from the speed-o-meter 61, for example. In response to these inputs, the logic circuitry 58 dynamically generates testing parameters, such as apertures for transmitting and receiving ultrasonic signals, the angle of transmission and reception of ultrasonic signals and the focal depth of the ultrasonic signals based on the inputs, via a computer program, for instance. The logic circuitry 58 communicates the testing parameters to the phased array ultrasonic unit 50, which activates the selected transducers elements of the phased array transducer 24 to test the rail 12.

In the testing apparatus 10, the phased array ultrasonic unit 50 communicates with a data acquisition module 62. The data acquisition module 62 comprises memory components to store received and generated data. For example, the data acquisition module stores data from the sensing devices (example, the speedometer) as well as inputs from the operator workstation 60. The data acquisition module 62 is located locally to the testing apparatus or located remotely. Processing circuitry 64 is coupled to the data acquisition module 62 and receives data from the data acquisition module 62 for processing. The processing circuitry 64 processes the data to analyze for defects in the rail 12. By way of example, the processing circuitry includes hardware and/or software components that facilitate the analysis. For instance, the processing circuitry is configured to receive data from a database, to correlate the received ultrasonic signals to known types of defects in the rail. The processing circuitry 64 communicates with the operator workstation 60 and receives commands and parameters from the operator workstation 60, for instance. The processing circuitry can be located at the testing apparatus or can be located remote to the testing apparatus.

The operator workstation 60 communicates with a display 66 and a printer 68. The operator workstation 60 is configured to display the data from the processing circuitry 64 via an image module 65, using the display 66. The image module 65 includes hardware and/or software and acts as an interface between the processing circuitry 64 and the display 66. The printer 68 facilitates the production of a hard copy of the defect data of the rail 12.

The testing apparatus 10 communicates with a network via network communication circuitry 70, which facilitates communications with network in accordance with a network communication protocol, e.g. TCP/IP, Bluetooth, radio frequency (rF), and cellular protocols. For instance, the testing apparatus 10 includes wireless communication circuitry 72, thereby facilitating wireless communications with remote systems and devices. Advantageously, the network communication circuitry 70 and the wireless communication circuitry 72 can facilitate remote control, operations and communications with respect to the testing apparatus 10. For instance, the communication circuitry facilitates location of the processing, logic and data acquisition circuitry at remote location with respect to testing apparatus. Indeed, many of the above-discussed components can communicate via the wireless circuitry, thereby facilitating remote location and operation of these components. The testing apparatus 10 also includes a global positioning system (GPS) 74 for identifying coordinates, i.e., locating a position of the testing apparatus 10 in the railroad network. The testing apparatus 10 also includes an odometer 76, which is mechanically coupled to the wheel 38 and electrically coupled to the processing circuitry 64. The odometer 76 registers the distance traveled from the preset starting point of the testing apparatus 10. Thus, the odometer 76 facilitates locating the coordinates of the testing apparatus 10 in cooperation with or in addition to the GPS system 74. Advantageously, the testing apparatus 10 is capable of communicating a detected defect based on the processed data from the processing circuitry 64 and its corresponding location based on the coordinate or position of the testing apparatus 10.

Figure 2:
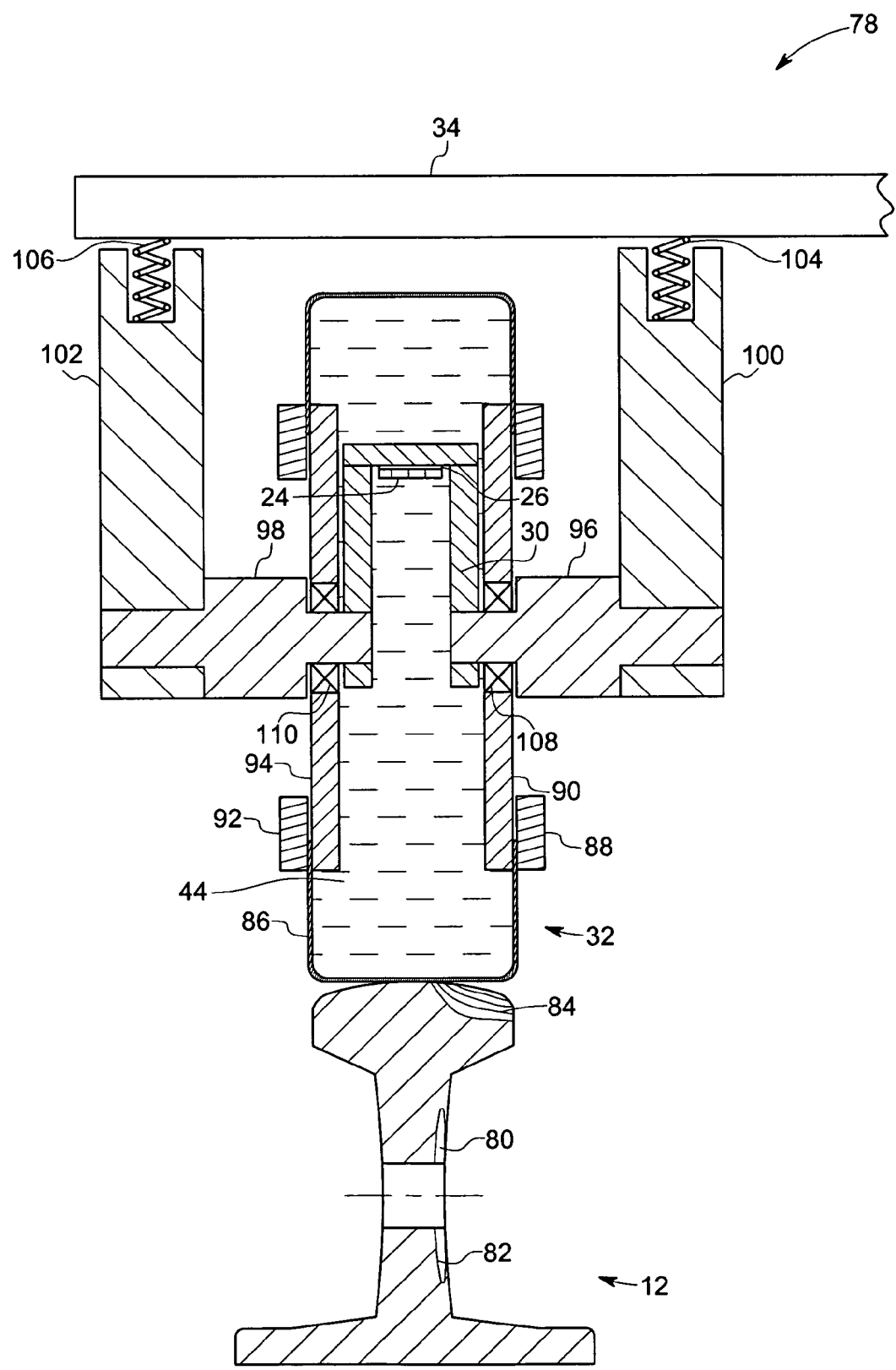
FIG. 2 is a partial and diagrammatic, cross-sectional view of a testing wheel having the phased array transducer of FIG. 1 along line 2-2.

FIG. 2 is a partial and diagrammatic cross-sectional view 78 of the rail 12 and the testing wheel 32 along line 2-2 of FIG. 1. As illustrated, the rail 12 may have bolthole defects 80 and 82 and/or a transverse defect 84. A flexible member 86 of the testing wheel 32 is disposed between plates 88, 90, 92 and 94. Fixed shafts 96 and 98 support the testing wheel 32. As discussed above, a bracket 30 is mounted to the shafts 96 and 98 to support the phased array transducer 24, which is housed in the housing 26. As depicted, the phased array transducer 24 is disposed away from the rail 12. Alternatively, the bracket can be mounted to the shafts 96 and 98 such that the phased array transducer 24 is disposed close to the rail 12. The shafts 96 and 98 are mounted to support 100 and 102 that are assembled to the carrier structure 34 through spring elements 104 and 106. In the testing apparatus, the spring elements 104 and 106 exert force on the testing wheel 32 to ensure proper contact and/or alignment of the testing wheel 32 with the rail 12. For example, spring elements 104 and 106 can also include a pneumatic system, a hydraulic system and/or a robotic system to exert force or to align the testing wheel 32. Advantageously, the spring elements 104 and 106 cooperate with a feedback mechanism to optimize the force exerted on the testing wheel 32. The wheel assembly 32 also includes bearings 108 and 110 that act as an interface between the testing wheel 32 and the shafts 96 and 98 and that facilitate rotational movement of the wheel 32 about the shafts. As discussed above, the testing wheel 32 is filled with the water based couplant 44 to facilitate improved transmission of ultrasonic signals between the phased array transducer 24 and the rail 12.

The testing apparatus 10, as described above in FIG. 1, facilitates the testing material integrity of various objects at high speeds. As discussed above, since the longitudinal axis of the phased array transducer is generally parallel to the longitudinal axis of the rail or the object being tested, the testing apparatus facilitates tests at speeds as high as 110 kilometers per hour (70 miles per hour) and beyond. In one embodiment, the object remains stationary, while the testing apparatus 10 moves relative to the object at high speeds as discussed above. In another embodiment, the testing apparatus 10 remains stationary, while the object moves at high speeds relative to the testing apparatus 10 to testing the object. Indeed, the testing apparatus facilitates the testing of plates, bars, tubes, billets and support structures, to name but a few objects.

Figure 3:
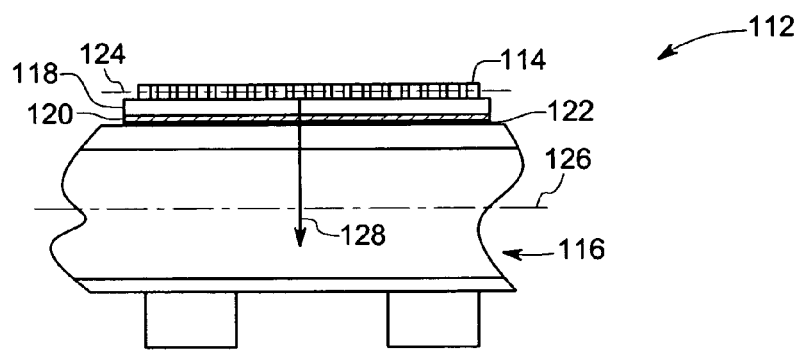
FIG. 3 is a diagrammatic representation of a testing apparatus having a phased array transducer for testing a rail, in accordance with an exemplary embodiment of present technique.

FIG. 3 is a diagrammatic representation of a testing apparatus 112 having a phased array transducer 114 for testing a rail 116, in accordance with an exemplary embodiment of present technique. As illustrated, the phased array transducer 114 is coupled to a substrate 118 that advantageously acts as a couplant to facilitate improved transmission and reception of ultrasonic signals to and from the rail 116. Advantageously, to mitigate a likelihood of damage, the testing apparatus 112 includes an anti-friction pad 120 disposed adjacent to the surface of the rail. Furthermore, a couplant 122, such as thin film of water, located between the testing apparatus 112 and the rail 116 facilitates the transmission of ultrasonic signals to and from the testing apparatus. As illustrated, a longitudinal axis 124 of the phased array transducer 114 and a longitudinal axis 126 of the rail 116 are generally parallel to one other and generally extend in the same direction. The phased array transducer 114 travels in a direction along the longitudinal axis 126 of the rail 116 to detect defects using longitudinal ultrasonic signals 128. As will be appreciated by those skilled in the art, longitudinal ultrasonic signals cause particles of the rail oscillate in the direction of propagation of the ultrasonic signals.

Figure 4:
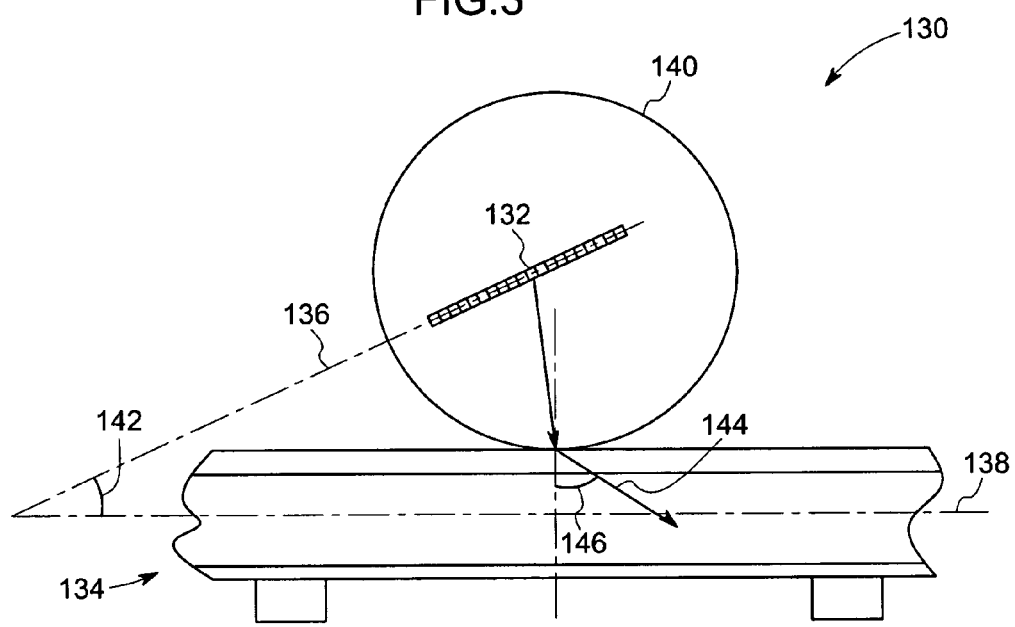
FIG. 4 is a diagrammatic representation of another testing apparatus having a phased array transducer for testing a rail, in accordance with an exemplary embodiment of present technique.

FIG. 4 is a diagrammatic representation of another testing apparatus 130 having a phased array transducer 132 for testing a rail 134, in accordance with an exemplary embodiment of present technique. The longitudinal axis of the phased array transducer is denoted by 136 and that of the rail is denoted by 138. The phased array transducer 132 is coupled to a testing wheel 140 in such a way that the longitudinal axis 136 of the phased array transducer 132 is at an angle, denoted by 142 to the longitudinal axis 138 of the rail 134. Although at an angle, the longitudinal axis of the phased array transducer extends generally in the direction of the longitudinal axis of the tested rail. The phased array transducer 132 detects defects in the rail 134 using mode converted shear ultrasonic signals 144. The angle, as denoted by 142, is selected in such a way that a desired angle of refraction of the shear ultrasonic signals, denoted by 146 is maintained. By way of example, the testing apparatus 130 is configured to transmit shear ultrasonic signals with various angles of refraction. Indeed, the testing apparatus 130, in certain embodiments, is configured to transmit shear ultrasonic signals with any desired angle of refraction, including 30 degrees, 40 degrees, 70 degrees, and 80 degrees. In the transverse or shear ultrasonic signals, particles of the rail oscillate at a right angle or transverse to the direction of propagation of the ultrasonic signals. Advantageously, shear ultrasonic signals increase the likelihood of detection of defects.

Figure 5:
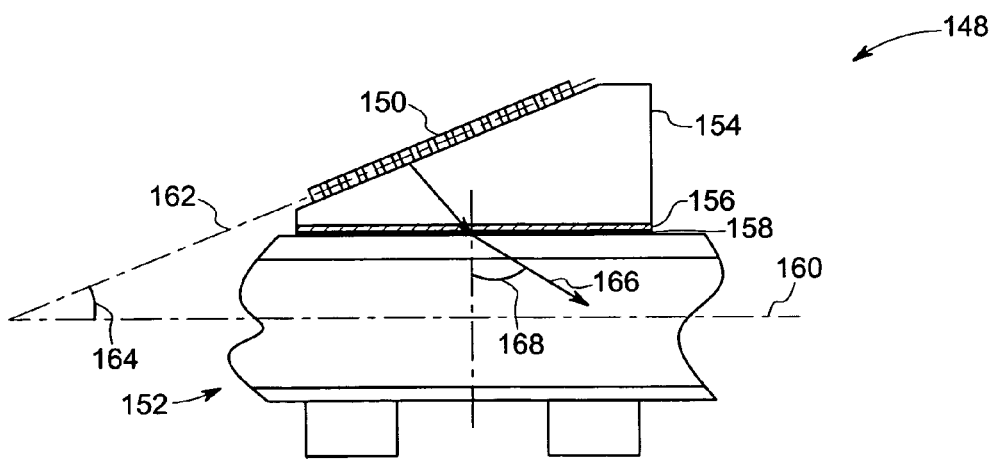
FIG. 5 is a diagrammatic representation of yet another testing apparatus having a phased array transducer for testing a rail, in accordance with an exemplary embodiment of present technique.

FIG. 5 is a diagrammatic representation of yet another testing apparatus 148 having a phased array transducer 150 for testing a rail 152, in accordance with another exemplary embodiment of present technique. The testing apparatus includes a wedge 154, an anti-friction pad 156 and a thin film of couplant 158. The testing apparatus 148 is configured to travel along a longitudinal axis 160 of the rail 152 to detect defects in the rail 152. As illustrated, the phased array transducer 150 is coupled in such a way that a longitudinal axis 162 of the phased array transducer 150 is at an angle, denoted by 164, with the longitudinal axis 160 of the rail 152. As discussed above, such an arrangement of the phased array transducer 150 facilitates the production of mode converted shear ultrasonic signals 166 with a desired angle of refraction, as denoted by 168. Typically the angle of refraction includes, but not limited to 30 degrees, 40 degrees, 70 degrees and 80 degrees.

During operation, the phased array transducer, as discussed above, is moved in a direction along the longitudinal axis of the rail to detect defects in the rail. During the movement, the phased array ultrasonic unit 50, based on various inputs, activates individual elements of the phased array transducer 150 to produce the desired signal. Additionally, the phased array ultrasonic unit 50 also activates certain individual transducers to receive the reflected signals. For the purposes of the present application, the transmitted signals and the reflected signals (i.e., the signals produced by reflecting the transmitted signals) are referenced as the different signals. As discussed further below, the activated transducers of a phased array transducer for producing a signal is referred to as transmit aperture. Similarly, the activated transducers of a phased array transducer for receiving the reflected signals are referred to as receive apertures.

Figure 6:
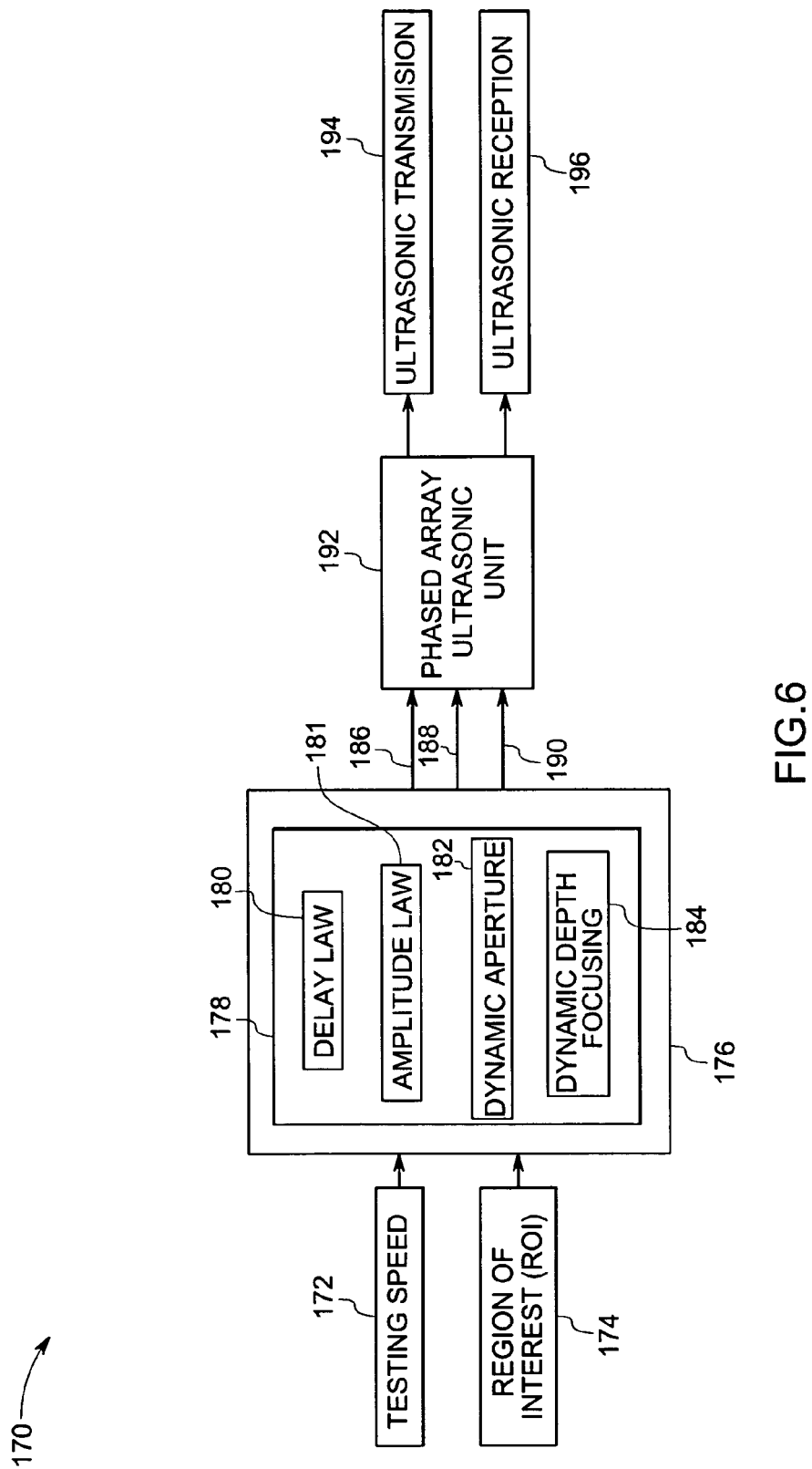
FIG. 6 is a diagrammatic representation of an arrangement for detecting defects in a rail, in accordance with an exemplary embodiment of present technique.

FIG. 6 is a diagrammatic representation of an arrangement 170 for transmission and reception of ultrasonic signals for detecting defects in a rail, in accordance with an exemplary embodiment of the present technique. The logic is conducted in the logic circuitry and/or the processing circuitry and is based on inputs received from various locations. For example, testing speed 172 and a region of interest 174 are the inputs that are fed to logic circuitry 176 by the speedometer and the user interface, respectively. For this discussion, the testing speed 172 is a relative speed between the testing apparatus and the rail or the object being tested. The application logic includes a focal law generator 178. The focal law generator 178 is operable as hardware or software and includes algorithms and/or algorithmic relationships for delay law 180, amplitude law 181, dynamic aperture 182 and dynamic depth focusing aspects 184 and/or combinations or permutations thereof. The two important parameters for focusing an array are the delays and the apodization (gain) of each element of the phased array. The set of delays is called delay law, and the set of gains is called amplitude law. By way of example, the delay law 180 computes the delay between received ultrasonic signals dynamically, by taking into account the inputs 172, 174 and the selected apertures. As discussed above, the dynamic aperture 182 identifies a set of elements of the phased array transducer to be active for transmission and another set of elements of the phased array transducer to be active for reception of ultrasonic signals. In other words, the dynamic aperture 182 determines apertures dynamically for transmitting and receiving ultrasonic signals based on inputs 172, 174 and the delay between the ultrasonic signals. As another example, the algorithms for dynamic depth focusing aspects 184 determine the depth to be focused based on the inputs 172 and 174. As can be seen, the algorithms for delay law, amplitude law, dynamic aperture and dynamic depth focusing aspects compute the parameters dynamically based on changes in the inputs 172 and 174. Thus the focal law generator 178 provides a set of instructions such as, apertures for transmitting and receiving the ultrasonic signals 186, a delay for each element of phased array transducer in transmitting and receiving ultrasonic signals 188 and a depth 190 for testing a rail. This set of instructions is then provided to a phased array ultrasonic unit 192, which activates the corresponding elements of the phased array transducer (see FIG. 1) for transmitting 194 and receiving 196 ultrasonic signals in an activation pattern or sequence. As one example, the activation pattern excites the transducer elements temporally in a direction that follows the testing direction or the longitudinal axis of the rail.

FIG. 7 is a diagrammatic representation of a testing apparatus 198 for performing dynamic focusing for testing material integrity of an object 200 during operation, in accordance with an exemplary embodiment of present technique. The testing apparatus 198 performs dynamic focusing based on the region of interest and the speed of the testing apparatus as inputs. For illustration, only two elements 202 and 204 of the phased array transducer are depicted. The first element 202 sends a first ultrasonic signal 206 towards a region of interest 208 in the object 200. Similarly, the second element 204 sends a second ultrasonic signal 210 towards the region of interest 208. As can be seen, the distance between the first element 202 and the region of interest 208 is greater than the distance between the second element 204 and the region of interest 208. Hence the elements 202 and 204 are excited in an activation pattern to ensure that the ultrasonic signals 206 and 210 reach the region of interest 208 at the same time, that is, activating the elements 202 and 204 with a delay between the first ultrasonic signal 206 and the second ultrasonic signal 210. Similarly, there is a delay in receiving a reflected ultrasonic signal 212 by the first element 202, compared to the second element 204, receiving a reflected ultrasonic signal 214. The reflected ultrasonic signals 212 and 214 thus received are added to analyze for defect in the object 200. Hence estimation of the delay in receiving the reflected ultrasonic signals 212 and 214 facilitates adding the reflected ultrasonic signals 212 and 214.

FIG. 8 is a graph 216 to illustrate the transmission of ultrasonic signals by phased array transducer elements of FIG. 7 as discussed above and with time delay, in accordance with aspects of present technique. The X-axis as denoted by 218 represents time and Y-axis as denoted by 220 represents the element number of the phased array transducer. The curve 222 represents the transmission of ultrasonic signal by the first element 202 at time, represented by 224. Similarly curve 226 represents the transmission of ultrasonic signal by the second element 204 at time, represented by 228. As can be seen, the delay 230 is the difference in time 228 and 224 between the transmission of ultrasonic signals 226 and 222 by the second element 204 and the first element 202 respectively.

FIG. 9 is a graph 232 to illustrate the reception of ultrasonic signals by phased array transducer elements of FIG. 7, with time delay, in accordance with aspects of present technique. The X-axis, as denoted by 234 represents time and the Y-axis, as denoted by 236 represents the element number of the phased array transducer. The curve 238 represents reception of ultrasonic signal by the first element 202 at time, represented by 240. The curve 242 represents reception of ultrasonic signal by the second element 204 at time, represented by 244. The delay 246 is the difference in time 240 and 244 between the reception of ultrasonic signals 238 and 242 by the first element 202 and the second element 204 respectively. In other words the elements 202 and 204 are activated with the delay 248 for receiving the ultrasonic signals. The received ultrasonic signals 238 and 242 are added as represented by the block 250 to generate a signal 252.

The signal 252 facilitates the detections of defects in the object 200. For example, as discussed above, the logic circuitry and/or the processing circuitry receive data from a database or a look-up-table (LUT), which includes data correlating received signal type to types of defects found in a rail. Accordingly, the received signals, when correlated with the data from the database or the LUT, provide indications of certain defects in the rail, for instance. Furthermore, deviations of the receive signals from expected norms also provides indications of a defect in the rail. Additionally, by selecting a desired region of interest in the rail, testing resources are focusable at desired areas in the rail, such as structurally weaker areas of the rail.

With FIGS. 1-9 in mind, FIG. 10 is a flowchart illustrating an exemplary process for detecting defects in a rail, in accordance with aspects of present technique. The process includes providing a set of inputs to a testing apparatus as in step 254. The input includes region of interest (ROI) in the rail to test for defects, which further includes an angle 256 and a depth 258 for transmitting and receiving ultrasonic signals. The input further includes estimating testing speed as in step 260. As discussed above, the testing speed is a relative speed between the testing apparatus and the rail or an object being tested.

The following few steps define a logic for transmitting ultrasonic signals towards the rail for testing the rail. As defined by a dynamic aperture control for transmission, a set of elements of a phased array transducer are identified and activated as in step 262. The next step is to calculate delays in transmitting ultrasonic signals by each identified element using delay law as in step 264. Then the phased array ultrasonic unit sends commands to transmit ultrasonic signals as in step 266.

Similarly the following few steps define a logic for receiving ultrasonic signals from the rail. Initially based on a dynamic aperture control for reception, a set of elements of the phased array transducer are identified and activated as in step 268. The next step is to receive ultrasonic signals with delays in between as defined by the receive aperture, from the region of interest in the rail as in step 270. The ultrasonic signals from each element are added based as in step 274.

The logic for transmitting and receiving ultrasonic signals as discussed above are repeated for various depths and angles as in steps 276 and 278 and the data is analyzed for defects in the rail as in step 280. As will be appreciated by those skilled in the art, the defects can be correlated to the corresponding location in the rail using the speed data or the position data.

As will be appreciated by those skilled in the art, the process steps as illustrated in FIG. 10 can also be employed to test material integrity of any object. As described earlier, either the testing apparatus or the object can move relative to the other to perform the testing. Thus the relative speed is provided along with the region of interest as inputs. The process steps for testing the material integrity of the object are substantially similar to those steps as described in FIG. 10.

FIG. 11 is a diagrammatic representation of an exemplary remote monitoring and field monitoring arrangement 282, in accordance with aspects of present technique. The rail testing apparatus 284 is coupled to a field monitoring system 286 and a remote monitoring system 288 through wireless communication circuitry 290. The testing apparatus 282 exchanges testing data with the field monitoring system 286 and the remote monitoring system 288.

As will be also appreciated, the above-described techniques may take the form of computer or controller implemented processes and apparatuses for implementing those processes. The above-described technique can also be embodied in the form of computer program code containing instructions for testing and detecting defects in rails. The computer program code may be embodied in tangible media, such as floppy diskettes, CD-ROMs, hard drives, or any other computer-readable storage medium. The computer program code is loaded into and executed by a computer or controller; the computer becomes an apparatus for practicing the technique. The disclosure may also be embodied in the form of computer program code or signal, for example, whether stored in a storage medium, loaded into and/or executed by a computer or controller, or transmitted over some transmission medium, such as over electrical wiring or cabling, through fiber optics, or via electromagnetic radiation, wherein, when the computer program code is loaded into and executed by a computer, the computer becomes an apparatus for practicing the technique. When implemented on a general-purpose microprocessor, the computer program code segments configure the microprocessor to create specific logic circuits.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A testing apparatus for testing material integrity of an object, the testing apparatus comprising:
   a phased array transducer disposed external to the object, wherein the phased array transducer is configured to transmit a first set of ultrasonic signals and to receive a second set of ultrasonic signals; and
   logic circuitry coupled to the phased array transducer and configured to dynamically control apertures for transmitting the first set of ultrasonic signals and receiving the second set of ultrasonic signals based on a region of interest and a testing speed.

2. The testing apparatus as recited in claim 1, wherein the object is configured to travel at high speeds to test material integrity of object.

3. The testing apparatus as recited in claim 1, wherein a longitudinal axis of the phased array transducer is parallel to a longitudinal axis of the object.

4. The testing apparatus as recited in claim 1, wherein a longitudinal axis of the phased array transducer is at an angle to a longitudinal axis of the object.

5. The testing apparatus as recited in claim 1, wherein the phased array transducer is configured to test material integrity using longitudinal ultrasonic signals or shear ultrasonic signals.

6. The testing apparatus as recited in claim 1, wherein the phased array transducer is configured to modify an angle of transmission of the first set of ultrasonic signals and an angle of reception of the second set of ultrasonic signals.

7. The testing apparatus as recited in claim 1, wherein the phased array transducer is configured to modify a focal depth of the first and second sets of ultrasonic signals.

8. The testing apparatus as recited in claim 1, further comprising processing circuitry configured to provide signals that are indicative of a defect in the object in response to communications from the phased array transducer.

9. A method for testing material integrity of an object, the method comprising:
   controlling a first aperture dynamically to transmit a first set of ultrasonic signals;
   transmitting the first set of ultrasonic signals towards a region of interest via the first aperture;
   controlling a second aperture dynamically to receive a second set of ultrasonic signals; and
   receiving the second set of ultrasonic signals from the region of interest via a second aperture based on the region of interest and a testing speed.

10. The method as recited in claim 9, further comprising dynamically focusing a plurality of ultrasonic signals towards the region of interest at a plurality of angles.

11. The method as recited in claim 9, further comprising dynamically focusing a plurality of ultrasonic signals towards the region of interest at a plurality of depths.

12. The method as recited in claim 9, further comprising adding the second set of ultrasonic signals to generate a signal indicative of defect in the object.

13. A testing apparatus for detecting defects in a rail, the testing apparatus comprising:
   means for dynamically controlling a first aperture for transmitting a first set of ultrasonic signals towards the rail;
   means for transmitting the first set of ultrasonic signals into the rail;
   means for dynamically controlling a second aperture for receiving a second set of ultrasonic signals from the rail; and
   means for receiving the second set of ultrasonic signals from the rail in response to the first set of ultrasonic signals based on the region of interest and a testing speed.

* * * * *